United States Patent [19]

Matsueda et al.

[11] Patent Number: 4,916,070
[45] Date of Patent: Apr. 10, 1990

[54] FIBRIN-SPECIFIC ANTIBODIES AND METHOD OF SCREENING FOR THE ANTIBODIES

[75] Inventors: Gary R. Matsueda, Winchester; Edgar Haber, Weston, both of Mass.

[73] Assignee: The General Hospital Corporation, Boston, Mass.

[21] Appl. No.: 851,514

[22] Filed: Apr. 14, 1986

[51] Int. Cl.⁴ .................. C12N 5/00; A61K 39/395; G01N 33/577
[52] U.S. Cl. .................. 435/172.2; 435/7; 435/240.27; 530/387; 530/808; 530/809; 935/90; 935/92; 935/103; 935/110; 935/107; 436/548; 424/85.8; 424/9
[58] Field of Search ............. 435/7, 13, 68, 172.2, 435/188, 240, 27, 948; 436/548, 808, 809, 811; 530/387, 808, 809; 424/1.1, 9, 85, 94.63; 935/90, 92, 103, 107, 110

[56] References Cited

U.S. PATENT DOCUMENTS 4,147,765  4/1979  Stephen et al.
4,245,040  1/1981  Pilgeram ............................ 435/13

OTHER PUBLICATIONS

Rosebrough et al., Radiology, 156:515-517, (Aug. 1985).
Sevilla et al., Fed. Proceed., 44(4): 1073, Abst. 3872, Mar. 5, 1985.
Bode et al., Science, 229: 765-767, Aug. 23, 1985.
Ito et al., Fed. Proceed., 44(6): Abst. 8381, pp. 1846, Mar. 12, 1985.
Bosnjakovic, V. B. et al., Lancet, 2:452, (1977).
Day, E. D. et al., J. Natl. Cancer Insti., 22:413, (1958).
Bale, W. F. et al., Cancer Res., 20:1488, (1960).
Bale, W. F. et al., Cancer Res., 40:2965, (1980).
Pressman, D., Cancer Res., 40:2960-2964, (1980).
Reich, T. et al., Surgery, 60:1211, (1966).
Spar, T. L. et al., Circulation Research, 17:322-329, (1965).
Knight, L. C. et al., J. Nuclear. Med., 19:891, (1978).
Ouchi, H. et al., Surgery, 51:42, (1962).
Hui et al., Science, 222:1129, (1983).
Kudryk, B. et al., Mol. Imm., 21:89, (1984).
Khaw et al., J. Nucl. Med., 26:21, (1985).

Primary Examiner—Ester M. Kepplinger
Attorney, Agent, or Firm—Saidman, Sterne, Kessler & Goldstein

[57] ABSTRACT

The invention relates to a method of screening for fibrin clot-specific monoclonal antibodies and to the monoclonal antibodies screened by this method. The invention also relates to immundiagnostic and immunotherapeutic applications of the screened fibrin clot-specific monoclonal antibodies.

7 Claims, 4 Drawing Sheets

IN-VITRO BINDING TO HUMAN CLOTS

FIBRIN-SPECIFIC ANTIBODIES AND METHOD OF SCREENING FOR THE ANTIBODIES

The present invention relates to a method of screening for fibrin clot-specific monoclonal antibodies and to the monoclonal antibodies screened by this method.

BACKGROUND OF THE INVENTION

In vivo immunodetection of thrombi and fibrin deposits remains an important clinical problem. In humans, the detection and localization of deep vein thrombi and coronary artery thrombi are two clinically important problems.

Blood clots when thrombin cleaves two pairs of small peptides from fibrinogen to yield fibrin monomers (Blomback, B. and Vestermark, A., *Ark. Kemi* 12: 173 (1958) and Doolittle, R. F., *Adv. Protein Chem.* 27: 1 (1973)). Fibrin monomers spontaneously aggregate to form an insoluble gel, which is then covalently stabilized by Factor XIIIa. Despite the dramatic differences between the two, fibrin retains 98% of the original covalent structure of fibrinogen. Thus, it is understandable that anti-fibrin serum cross-reacts strongly with fibrinogen, and that only one instance is known where a fibrin-specific serum was produced (Bosnjakovic, V. B. et al., *Lancet* 2: 452 (1977)).

Polyclonal antibodies raised against fibrin or fibrinogen have been utilized for localizing a variety of tumors, in particular the fast-growing kind (Day, E. D. et al., *J. Natl. Cancer Inst.* 22: 413 (1958), Bale, W. F. et al., *Cancer Res.* 20: 1488 (1960), Pressman, D., *Cancer Res.* 40: 2965 (1980)). However, these antibodies all showed to some extent cross-reactivity with fibrinogen.

Polyclonal antibodies to fibrin-fibrinogen, to fibrinogen alone or to degradation products of both polypeptides have been developed for use in the detection of venous thrombosis in humans (Reich, T. et al., *Surgery* 60(6): 1211, Spar, I. L. et al., *Circulation Research*, XVII: 322 (1965), and Stephan, W. et al., U.S. Pat. No. 4,147,765). In Reich, T. et al. and Spar, I. L. et al., supra, the radiolabelled antibodies had a substantial degree of fibrin-fibrinogen cross-reactivity. In the Stephan, W. et al. reference, the antiserum was elicited by immunological challenge with the early fibrin and fibrinogen degradation products formed by the action of plasmin on fibrin and fibrinogen, and referred to in the literature as fibrinogen S (fg-X), and fibrinogen Y (fg-Y).

A different approach for the detection of deep-vein thrombosis was undertaken by Knight, L. C. et al., *J. Nuclear Med.* 19(8): 891 (1978) by radio-iodinating fibrinogen. This method, however, was found to be inferior to the labelling of platelets with $^{111}$In, for the localization of thrombi in deep-vein thrombosis.

When plasminogen is converted by an activator to plasmin, the active fibrinolytic enzyme of plasma, it develops a marked affinity for its substrate, fibrin. Ouchi, H. and Warren, R., *Surgery* 51(1): 42 (1962), discovered that this affinity might be put to use by tagging plasminogen with a radioactive isotope and using it as a tracer to seek out intravascular clots. However, the $^{131}$I-labelled plasminogen showed a somewhat depressed fibrinolytic activity (28.6%).

Pilgeram, L., U.S. Pat. No. 4,245,040 improved on an earlier method for detecting circulating fibrin (Lorand, L., in *Fibrinogen and Fibrin Turnover of Clotting Factors*, Ed. Koller F., F. K. Schattauer Verlag-Stuttgart, 1963; and Kisker, C. D. and Rush, R., in "Detection of Intravascular Clotting," *J. Clin. Investig.* 50:2235 (1971)). Pilgeram's improvement consisted in attaching an isotopic label to the soluble circulating fibrin, by means of a Factor XIII-containing glycine-$C^{14}$ ethyl ester. However, it is recognized that the use of antifibrin antibodies which cross-react with fibrinogen is limited.

Monoclonal antibodies specific against fibrin have been described in Hui et al., *Science*, 222: 1129 (1983). Further description of the same type of antibodies can be found in commonly assigned co-pending U.S. application, Ser. No. 824,228, filed January 30, 1986, for "Fibrin-Specific Monoclonal Antibodies Lacking Fibrinogen Cross-Reactivity." Other examples of antibodies with a specificity against a thrombus include Kudryk et al., *Mol. Imm.*, 21: 89 (1984); European Patent Application 146,050 to Callewaert, published June 26, 1985, for "Site Selective Plasminogen Activator and Method of Making and Using Same;" and Australian Patent Application, AV-A-25387/84 to Bundesen et al., for "Monoclonal Antibodies with Specificity for Cross-linked Fibrin and Their Diagnostic Uses."

A need continues to exist for highly specific antifibrin monoclonal antibodies and for synthetic epitopic peptides capable of raising such nonfibrinogen-cross-reacting antibodies. The antibodies would be useful for the in vivo detection of thrombi.

SUMMARY OF THE INVENTION

The present invention relates to a method of screening for fibrin-specific antibodies and to fibrin-clot specific monoclonal antibodies screened by this method.

The method of screening for the fibrin-specific antibodies uses completely cross-linked fibrin for the selection of antibodies that preferentially bind to clotted fibrin. The fibrin-clot specific monoclonal antibodies screened by this method are secreted from hybridoma cell lines capable of secreting monoclonal antibodies against fibrin, without fibrinogen cross-reactivity. The inventors have found that the use of the cross-linked fibrin clot provides fabrin-clot specific monoclonal antibodies that have increased binding to in vitro and in vivo thrombi. Generally, in the method of screening, the whole purified clot is immobilized to a solid support. The hybridoma culture medium, containing the fibrin-specific monoclonal antibodies, is contacted with the immobolized clot. The fibrin-specific monoclonal antibodies may then be detected and screened by radio-immunoassay or by enzyme-linked immunosorbent assay (ELISA).

The fibrin-clot specific antibodies screened by this method are useful for the in vitro and in vivo detection of thrombi and fibrin deposits in humans and animals. These monoclonal antibodies may also be used in complexes with thrombolytic agents.

DETAILED DESCRIPTION OF THE INVENTION

The antibodies that may be screened according to method of this invention may be any antibodies which are fibrin-specific and are substantially devoid of fibrinogen cross-reactivity. For example, antibodies with that specificity have been described in Hui, K. Y. et al., *Science*, 222:1129–1131 (1983). Further description of the same type of antibodies can be found in commonly assigned co-pending U.S. patent application Ser. No. 824,228, filed January 30, 1986, by Gary R. Matsueda et al. for "Fibrin-Specific Monoclonal Antibodies Lacking Fibrinogen Cross-Reactivity." Other types of fibrin-specific monoclonal antibodies include those of Kudryk et al., supra, Callewaert, supra, and Bendesen et al., supra, all of the foregoing references incorporated herein by reference.

The aforementioned co-pending patent application, for example, describes antibodies and methods of preparing the same of the specificity desired in the present invention, by providing peptides capable of raising such antibodies. These peptides generally are those comprising the formula:

A is gly; B is His or Pro; C is Arg; D is Pro or Val; E is Leu or Val; F is Asp or Glu; and G is Lys or Arg; (These residues can be in their protected or unprotected form, as is otherwise understood to those of skill in the art. Appropriate amino, or carboxyl protecting groups can be used (see below).)

$R^1$ is $R^2$; lys-CO—$R^2$; -lys-arg CO $R^2$; or -lys-arg-glu-CO—$R^2$;

$R^2$ is -cys-COR$^3$, OH, OM or NR$^4$R$^5$;

$R^3$ is OH, OM or NR$^4$R$^5$.

M is a pharmaceutically acceptable cation or a lower ($C_1$-$C_6$) branched or unbranched alkyl group;

$R^4$, $R^5$ are the same or different and selected from the group consisting of H or a lower alkyl group.

In other words, the compounds are peptides containing 7 to 11 amino acid residues as defined above. The preferred compounds are the peptides having 7 to 8 amino acid residues wherein $R^1=R^2=$OH, OM or —NR$^4$N$^5$; or $R^1=R^2=$cys-CO—$R^3$ where $R^3$ is OH, OM or —NR$^4$R$^5$.

When the C- terminal residue is a cysteine, the same may be substituted at the -S atom with an immunogenic protein, such as albumin, or hemocyanin. Preferred substitution is with maleimidobenzoyl or maleimidobenzoyl-keyhole limpet hemocyanin.

Useful cations M are alkaline or alkaline earth metallic cations (i.e., Na, K, Li, ½ Ca, ½ Ba, etc.) or amine cations (i.e., tetraalkyl ammonium, trialkylammonium, where alkyl can be $C_1$-$C_{12}$).

The variable length peptides may be in the form of the free amines (on the N-terminus), or acid-addition salts thereof. Common acid-addition salts are hydrohalic acid salts, i.e., HBr, HI, or more preferably, HCl.

The variable length peptides of this invention can be in the linear form or, in addition they may be in the form of a cyclic peptide.

Representative peptides for use as immunogens in the present invention are:

The peptides can be synthesized by the well known solid phase peptide synthesis described by Merrifield, *J. Am. Chem. Soc.* 85:2149 (1962) and Steward and Young in *Solid Phase Peptides Synthesis* (Freeman, San Francisco, 1969) pp. 27–62, using a copoly(styrenedivinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of the appropriate fractions of the column will yield the homogeneous peptide or their derivatives, which are then characterized by amino acid analysis, thin layer chromatography, high performance liquid chromatography, ultraviolet absorption spectroscopy, molar rotation, solubility, and quantitated by the solidphase Edman degradation (Matsueda, G. R., Haber, E. and Margolies, M. N., *Biochemistry* 20: 2571 (1981)).

The technique of synthesis and isolation is fully described in the aforementioned references, as well as in U.S. Pat. No. 4,269,827, which is herein incorporated by reference. It is to be noted that during or after the synthesis, cysteines may preferably be blocked by 3,4-dimethylbenzyl (DMB), arginines and histidines by tosyl (TOS), aspartic acid and glutamic acids by benzyl (Bzl), and lysines by 2-chloro-benzyloxycarboxyl (2-CBZ). Other protective blocking groups are well-known, and can be used in the present invention.

The techniques of sensitization and/or immunization, cell fusion, ascites production, selection of mixed hybridomas, or subcloning of monoclonal hybridomas are generally well known in the art. Attention, for example, is brought to Koprowski et al., U.S. Pat. No. 4,172,124, Koprowski et al., U.S. Pat. No. 4,196,265, Wands et al., U.S. Pat. No. 4,271,145, or Douillard, J. Y. and Hoffman, T., *Basic Facts about Hybridomas*, in *Compendium of Immunology*, Vol. II, L. Schwartz, ed. (1981), which are herein incorporated by reference.

In general, the purified epitopic peptides containing fibrin-specific sequences, have attached at the C-terminus a cysteine, to permit unidirectional attachment of the synthetic peptide to an immunogenic protein through a connecting bridge, e.g., maleimidobenzoylated (MB)-keyhole limpet hemocyanin (KLH). Other immunogenic conjugates can also be used, e.g., albumin, and the like. The resulting structure may have several peptide structures linked to one molecule of protein.

Lines of somatic cells immunized against the synthetic peptides can be obtained by any suitable immunization technique. The host is sensitized by administering the antigen, usually in the form of a protein conjugate, as hereinbefore indicated, by any suitable method, preferably by injection, either intraperitoneally, intravenously, subcutaneously, or by intra-foot pad. Adjuvants may be included in the immunization protocol. Virus, bacteria or other cells may also be employed.

The initial immunization with the protein bound antigen can be followed by several booster injections given periodically at intervals of several weeks. Immunized somatic cells are then obtained periodically from the host by procedures well known to those skilled in the art. The antibody contained in the plasma of each host can then be tested for its fibrin-specificity and/or lack of fibrinogen cross-reactivity. The host having the highest antifibrin response is usually most desirable as the donor of the antibody secreting somatic cells. Hyperimmunization can be effected by repeatedly injecting the additional amounts of peptide-protein conjugate by intravenous and/or intraperitoneal route.

The immunized somatic cells, preferably spleen cells, must then be fused with another cell line to produce hybridomas capable of secreting antifibrin-specific antibodies which do not cross-react with fibrinogen. Some of the factors to be considered in the selection of another cell line for fusion are rapid, uniform growth characteristics, metabolic deficiency for growth in a specified component of the growth medium, and potential for good fusion frequency. Malignant cells have been found to be particularly suitable for fusion. The species from which such cell lines are derived is also an important factor. Several cell lines including mouse, rat, hamster and human myeloma lines are available and are preferred for obtaining hybridomas. A variety of fusing agents may be employed to induce cell fusion. Polyethylene glycol and virus-induced fusions are particularly efficacious and are the preferred agents.

Preferred conditions for the somatic cell fusion and establishment of the hybridoma cell lines are those reported by Kohler and Milstein, *Nature* (London) 256:496 (1975), which is herein incorporated by reference.

Preferred hosts for the production of somatic cells are mouse, in particular BALB/c, or AJ. Particularly suited malignant cells for the purpose of establishing hybridoma cell lines by somatic cell fusion are myeloma cell lines, in particular the Sp2/0 and NS-1 lines.

Rapid identification of hybridomas secreting the desired monoclonal antibody is a key procedure in all hybridoma work. Previously, fibrin-specific hybridomas have been screened using, inter alia, fibrin monomers. The inventors have discovered that using cross-linked fibrin clot for screening of hybridoma antibodies to select those hybridomas that secrete monoclonal antibodies specific against fibrin results in the selection of antibodies with increased fibrin-specific specificity. As used herein, the clot antigen is referred to as "crosslinked fibrin clot" or "minclot." In the method according to this invention, the screening assay comprises the following steps. First, coating a suitable surface support with cross-linked fibrin clot antigen such that the clot is immobilized on the support. Second, contacting the immobilized clot with the hybridoma culture medium that contains the secreted monoclonal antibody. Third, screening the clot antigen/monoclonal-fibrin specific antibody complex by use of a detectable label step. Detectable labelling steps that may be used in this invention include, but are not limited to, radioimmunoassays, enzyme immunoassays, fluorescent immunoassays, and chemiluminescent immunoassays. These assays are well known in the art. Detectable labels are described hereinbelow.

For example, in the radioimmunoassay, the whole clot is immobilized on microtiter wells. The hybridoma antibody sample is contacted with the clot-coated wells. After an incubation time and wash, the clot antigen/antibody complex is contacted with radiolabeled anti-Fab fragment antibody. After rinsing and drying the wells, the radioactivity is determined in a gamma counter. (Klinman et al., *Ann. Immunol.* (*Paris*), 127C:489 (1976), incorporated herein by reference.)

Enzyme-linked immunosorbent assay (ELISA) for detection of hybridoma antibodies to purified whole clot can also be used in the method of this invention. Typically the enzyme used will be peroxidase conjugated to an anti-Fab fragment antibody. The purified whole clot is immobolized on a microtiter well. Hybridoma antibody culture fluid is added to each of the clot antigen wells. After incubation and subsequent wash cycle, an appropriate dilution of peroxidase-conjugated anti-Fab fragment is added. Enzyme-linked immunoglobulin binding is detected using color reagents, such as $H_2O_2$ and o-dianisidine solution. Color intensity can then be measured using a photometer.

After the hybridoma cells secreting the fibrin-specific monoclonal antibodies have been screened, the positive fibrin-specific hybridoma cell lines can be selected and hybridoma clones grown. By cloning is meant the process of achieving growth of a cell line from a single parental cell, viz., a monoclonal expansion. Such cloning may be achieved by any suitable technique, such as by agarose technique and the like.

Antibody secreting hybrids grown in tissue culture flasks yield supernatants with variable concentrations of antibody, usually in the range of about 1-30 ug/ml. Higher yields are, therefore, obtained preferably by transferring hybrids into animals with inflammatory ascites. Ascites are preferably induced by intraperitoneal injection of the hybridoma or by other suitable methods.

Preservation of the hybridoma is important and may be accomplished by any suitable technique. A preferred method is by subcloning or by freezing adequate amounts of the hybridoma early after fusion, and to reclone the cell population, as needed.

The term "hybridoma," as used herein, refers to hybrid cells obtained by the technique of somatic cell fusion, as described in the specification, the hybrid so obtained having the capability of producing antifibrin-specific antibodies lacking fibrinogen cross-reactivity.

The term "fibrin-clot monoclonal antibodies," as used herein, refers to antibodies produced by a homogenous line of a cloned colony of cells, derived from a single parental hybridoma and screened by the method of this invention using a cross-linked fibrin clot.

Once the selected hybridoma has been cloned, it is a matter of routine in the art to isolate the fibrin-specific monoclonal antibodies produced or secreted from the hybridomas. Well known techniques, such as salt precipitation, gel chromatography, ion exchange chromatography, affinity chromatography, and the like, can be used to obtain the antibodies in substantially pure form.

By "substantially pure form," it is meant that the antibodies are essentially free from non-monoclonal antibody impurities, such as other proteins, other antibodies having different specificities, nucleic acids, polysaccharides, cell fragments, and the like. The antibodies can be used in soluble form or can be immobilized on an aqueous and soluble solid-phase, to obtain insolubilized antibodies.

The term "epitope," as used herein, refers to specific amino acid sequences characteristic of a protein, in which sequences arranged in a characteristic configuration can elicit antibodies which bind specifically to said sequences, in the configuration in which they appear (e.g., fibrin molecule), said antibodies not being capable of binding to the same amino acid sequence when it appears in a different configuration (e.g., fibrinogen molecule).

The fibrin-clot specific antibodies screened according to the method of this invention exhibit a higher degree of binding to in vitro and in vivo thrombi than those screened with fibrin or plasmin fragments. Hybridoma cell line, 5D7, using the methods described above and screened by the method of this invention, has been placed on deposit at the American Type Culture Collection (ATCC) in Rockville, Maryland, on April 14, 1986 and assigned the following number: ATCC HB 9087.

The antibodies produced by the method of the present invention can be utilized in any of a myriad of applications normally described for such antibodies. For example, these antibodies can be used in the development of a radioimmunoassay or enzyme-linked immunoassay for fibrin in the presence of fibrinogen or other proteins. They can most preferably be used as immunoaffinity ligands for the purification of fibrin. They can also be used for the in vitro detection of fibrin in clinical samples, for the in vivo localization of vascular thrombi or fibrin deposits, in linkage to drugs, and the like.

One or more of the monoclonal antibodies of the invention are particularly suited for use in in vitro and in vivo immunodiagnosis. For in vitro diagnosis the antibodies can be utilized in liquid phase or bound to a solid phase carrier. In addition, the monoclonal antibodies in these immunoassays can be detectably labeled in various ways.

There are many carriers to which the monoclonal antibodies of the invention can be bound and which can be used in detecting the presence of the fibrin. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for purposes of the invention. Those skilled in the art will know many other suitable carriers for binding monoclonal antibodies or will be able to ascertain such, using routine experimentation.

The term "antibodies" as used in this invention is meant to include intact molecules as well as fragments thereof, such as for example, Fab and F(ab')$_2$, which are capable of binding antigen.

There are many different labels and methods of labeling known to those of ordinary skill in the art. Examples of the types of labels which can be used in the present invention include enzymes, radioistopes, fluorescent compounds, chemiluminescent compounds, bioluminescent compounds, and metal chelates. Those of ordinary skill in the art will know of other suitable labels for binding to the monoclonal antibodies, or will be able to ascertain such, using routine experimentation. Furthermore, the binding of these labels to the monoclonal antibodies can be done using the standard techniques common to those of ordinary skill in the art.

One of the ways in which a monoclonal antibody of the invention can be detectably labeled is by linking the monoclonal antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label are malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

The presence of the detectably labeled monoclonal antibody can also be detected by labeling the monoclonal antibody with a radioactive isotope. The presence of the radioactive isotope can then be determined by such means as the use of a gamma counter or a scintillation counter. Isotopes which are particularly useful are $^3H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$, and $^{75}Se$.

It is also possible to detect the binding of detectably labeled monoclonal antibodies by labeling the monoclonal antibody with a fluorescent compound. When the fluorescently labeled monoclonal antibody is exposed to light of the proper wavelength, its presence can then be detected due to the fluorescence of the dye. Among the most commonly used fluorescent labeled compounds are fluorescein isothiocyanate, rhodamine, phycoerythrin, phycocyanin, allophycocyanin, o-phthalaldehyde, and fluorescamine.

The monoclonal antibodies of the invention can also be detectably labeled using fluorescence emitting metals such as, $^{152}Eu$, or others of the lanthanide series. These metals can be attached to the antibody molecule using such metal chelating groups as diethylenetriaminepentaacetic acid (DTPA) or ethylene diaminetetraacetic acid (EDTA).

Another way in which the monoclonal antibody can be detectably labeled is by coupling it to a chemiluminescent compound. The presence of the chemiluminescent-tagged monoclonal antibody is then determined by detecting the presence of luminescence that arises during the course of the chemical reaction. Examples of particularly useful chemiluminescent labeling compounds are luminol, isoluminol, aromatic acridinium ester, imidazole, acridinium salt, and oxalate ester.

Likewise, a bioluminescent compound may also be used to label the monoclonal antibody. Bioluminescence is a special type of chemiluminescence which is found in biological systems and in which a catalytic protein increases the efficiency of the chemiluminescent reaction. The presence of the bioluminescently labeled monoclonal antibody would be determined by detecting the presence of luminescence. Important bioluminescent compounds for purposes of labeling are luciferin, luciferase, and aequorin.

For purposes of the invention, the fibrin which is detected by antibody of the invention may be present in biological fluids and tissues. Any sample containing a detectable yet unknown amount of fibrin can be used. Normally, a sample is a liquid such as, for example, urine, saliva, cerebrospinal fluid, blood, serum and the like, or a solid or semi-solid such as for example, tissues, feces, and the like.

Another technique which may also result in greater sensitivity consists of coupling the antibodies to low molecular weight haptens. These haptens can then be specifically detected by means of a second reaction. It is common, for example, to use such haptens, as biotin (reacting with avidin) or dinitrophenyl, pyridoxal, and fluorescamine (reacting with specific antihapten antibodies) in this manner.

For diagnostic in vivo imaging, the type of detection instrument available is a major factor in selecting a given radionuclide. The radionuclide chosen must have a type of decay which is detectable for a given type of instrument.

Another important factor in selecting a radionuclide for in vivo diagnosis is that the half-life of the radionuclide be long enough so that it is still detectable at the time of maximum uptake by the target, but short enough so that after diagnosis unwanted radiation does not remain in the host. Ideally, a radionuclide used for in vivo imaging will lack a particulate emission, but produce a large number of photons in the 140–200 keV range.

For in vivo diagnosis and/or imaging radionuclides may be bound either directly or indirectly by using an intermediary functional group. An intermediary group which is often used to bind radioisotopes which exist as metallic cations to antibodies is DTPA. Typical examples of metallic ions which can be bound to antibody molecules and used for in vivo diagnosis are $^{99m}$Tc, $^{123}$I, $^{131}$I, $^{111}$In, $^{97}$Ru, $^{67}$Cu, $^{67}$Ga, $^{68}$Ga, $^{72}$As, $^{89}$Zr, and $^{201}$Tl.

The monoclonal antibodies of the invention can also be labeled with paramagnetic isotopes for purposes of in vivo diagnosis. Examples of elements which are particularly useful (as in Magnetic Resonance Imaging (MRI) techniques) in this manner are $^{157}$Gd, $^{55}$Mn, $^{162}$Dy, $^{52}$Cr, and $^{56}$Fe.

The dose ranges for the administration of the antibody are those large enough to detect the presence of thrombi. The dosage should not be so large as to cause adverse side effects, such as unwanted cross reactions, and anaphylactic reactions and the like. Generally, the dosage will vary with the age, condition, sex, and extent of disease in the patient, counter indications, if any, immune tolerance and other such variables, to be adjusted by the individual physician. Dosage can vary from 0.01 mg/kg to 500 mg/kg, preferably 0.01 mg/kg to 200 mg/kg. The antibody(ies) can be administered parenterally by injection or by gradual perfusion over time. It can be administered intravenously, intraperitoneally, intramuscularly, or subcutaneously.

Preparations for parenteral administration include sterile aqueous or non-aqueous solutions, suspensions, and emulsions. Examples of non-aqueous solvents are propylene glycol, polyethylene glycol, vegetable oil such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intraveneous vehicles include fluid and nutrient replenishers, electrolyte replenishers, such as those based on Ringer's dextrose, and the like. Preservatives and other additives may also be present, such as for example, antimicrobials, antioxidants, chelating agents, and inert gases and the like. See, generally, *Remington's Pharmaceutical Science*, 16th ed., Mac Eds., 1980.

The monoclonal antibodies of the invention are ideally suited for the preparation of a kit. Such a kit may comprise a carrier means being compartmentalized to receive in close confinement one or more container means such as vials, tubes, and the like, each of said container means comprising the separate elements of the immunoassay or imaging method to be used. The types of immunoassays which can be incorporated in kit form are many. Typical examples of some of the immunoassays which can utilize the antibodies of the invention are competitive immunoassays and immunometric, or sandwich immunoassays.

Monoclonal antibodies of the invention for in vivo purposes may be present in a kit in detectably labeled form or may be detectably labeled at some later time. For example, such a kit can contain the monoclonal antibodies of the invention coupled to a chelating group such as DTPA, and at time of use these antibodies are mixed with a metallic ion, such as $^{99m}$Tc to detectably label the monoclonal antibodies. In this way, a radioisotope with short half-life can be more effectively and economically utilized.

The fibrin-clot specific antibodies of this invention may also be used to produce therapeutic products obtained by coupling antibodies to thrombolytic agents.

By the terms "thrombolytic agent" as used herein is meant to include broadly any agent utilized for or inducing or initiating the lysis of a thrombus. The most common agents are urokinase, streptokinase and tissue-type plasminogen activator (TPA). Nevertheless, the obtainment of great selectivity observed with the antibodies utilized in the present invention, indicates that any other such thrombolytic agents can be utilized.

The term "couple" as utilized herein is meant to include broadly the firm attachment of the thrombolytic agent to the antibody. Such attachment may be covalent or noncovalent, although it is preferably covalent. The coupling of the two entities may be direct or, most commonly, by means of a coupling or conjugating agent. There are several intermolecular cross-linking reagents which can be utilized (see, for example, Means, G. E. and Feeney, R. E., *Chemical Modification of Proteins*, Holden-Day, 1974, pp. 39–43). Among these reagents are, for example, N-succinimidyl 3-(2-pyridyldithio) propionate (SPDP) or N-N'-(1,3-phenylene) bismalemide (both are highly specific for sulfhydryls, and form irreversible linkages); N-N'-ethylene-bis-(iodoacetamide) or other such reagent having 6 and 11 carbon methylene bridges (relatively specific for sulfhydril groups); 1,5-difluoro-2,4-dinitrobenzene (forms irreversible linkages with amino and tyrosine groups); p,p'-difluoro-m-m'-dinitrodiphenylsulfone (forms irreversible cross-linkages with amino and phenolic groups); dimethyl adipimidate (specific for amino groups); phenyl-2,4-disulfonylchloride (reacts principally with amino groups); hexamethylenediisocyanate or diisothiocyanate, or azophenyl-p-diisocyanate (reacting principally with amino groups); glutaraldehyde (reacting with several different side chains) and bis-diazobenzidine (reacting primarily with tyrosine and histidine). These are only a few of several cross-linking agents that can be utilized.

The conditions and concentrations useful for obtaining the antibody/thrombolytic agent couples of the invention can be readily adjusted by those of skill in the art by reference to known literature or by no more than routine experimentation.

The molar ratio of thrombolytic agent to antibody can vary from 1:10 to 100:1, preferably 1:1 to 100:1.

The coupled products of the invention can be formulated in appropriate pharmaceutical compositions by including thrombolytic amounts of the desired product together with pharmacologically appropriate carriers. Generally speacking, these carriers include aqueous or alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, such as those based on Ringer's, dextrose, and the like. Preservatives and other additives can also be present, such as, for example, antimicrobials, antioxidants, chelating agents, inert gases, and the like. See, generally, *Remington's Pharmaceutical Sciences,* 16th Ed., Mack, eds. 1980.

The coupled products of the invention can be administered to any patient in need of thrombolytic therapy. The administration can be any appropriate mode, including parenteral, intravenous, intramuscular, intraperitoneal, or, also appropriately, by direct infusion with a catheter, such as in intracoronary administration. The dosage and frequency of administration will depend on the age, sex and condition of the patient, concurrent administration of other drugs, counter indications and other parameters to be taken into account by the clinician.

The dosages and frequency of administration can be comparable to those used for the thrombolytic agents in the prior art. Generally, however, the dosage will be from about 0.001 to 0.2 times the dosage normally utilized for the thrombolytic agents by themselves.

For example, for the urokinase/antibody complex, the administration for systemic fibrinolysis (pulmonary embolism) values for a 75 kilogram person will be:
1. Loading dose: broad range: 150 to 66,000 units over 10 minutes; intermediate range: 330 to 30,000 units over 10 minutes.
2. Maintenance dose: broad range: 187.5 to 66,000 units per hour for 12 to 24 hours; intermediate range: 330 to 37,500 units per hour for 12 to 24 hours resulting in 2,400–1,650,000 total units (Sharma et al., *NEJM,* 306:1268–1276 (1982).

For the urokinase/antibody complex, the intracoronary administration dosage will be:
1. No loading dose.
2. 6–1,200 units per minute for 60–120 minutes resulting in a total of 360–144,000 units solution of 1.5–300 units per ml (Tennant et al., *Circulation,* 69:756–760 (1984)).

For the streptokinase/antibody complex, the systemic intracoronary administration dosage will be:
1. Loading dose: 250–50,000 units.
2. Maintenance dose: 100–20,000 units per hour for 24 hours or boluf injection of 5,000–300,000 units over 30 to 60 minutes.

For the streptokinase/antibody complex, the intracoronary administration dosage will be:
1. Loading dose: 0.01–6,00 units in 3 ml 5% dextrose over 2 minutes.
2. Maintenance dose: 5–1,000 units in one ml 5% dextrose up to maximal dose (500 to 100,000 units) (Laffel and Braunwald, *NEJM,* 311:710–717 (1984)).

In the aforementioned dosage descriptions, the term "units" refers to the known and established definitions utilized for the activity of the thrombolytic agents in the prior art.

The fibrin-clot specific antibodies of this invention may also be used to produce heterobifunctional antibodies as described in co-pending U.S. patent application, Ser. No. 851,554, filed concurrently herewith.

Having now generally described this invention, the same will become more readily understood by reference to specific examples included herein for purposes of illustration only, and is not intended to be limiting unless otherwise specified.

EXAMPLE I

When fibrinogen, a soluble 340,00 dalton plasma protein, is enzymatically cleaved by thrombin, an insoluble fibrin gel is formed as a primary event in the clotting of blood. During gelation, the clot is covalently stabilized by another enzyme, Factor XIIIa, which forms epsilon(gamma-Glutamyl)Lysyl bonds between adjacent fibrin (monomer) molecules. Although this transformation has been extensively studied, the detailed orientation of adjacent fibrin molecules within the crosslinked matrix remains unknown.

On the premise that antifibrin antibodies selected for their ability to bind to fibrin monomers might not bind optimally to fully crosslinked fibrin, a different immunochemical strategy was adopted. Instead of using dissociated fibrin monomers as antigen for the antibody selection process, completely crosslinked fibrin was used for selection of antibodies which bind preferentially to clotted fibrin.

For this purpose, a solution of purified human fibrinogen (Kabi, Grade L) was clotted with bovine thrombin in the presence of Factor XIIIa. To permit ease of manipulation, clots were formed within wells of flexible microtiter plates (Falcon brand from Becton-Dickinson). After the clots had formed, test solutions containing antibodies were carefully pipetted into wells containing crosslinked human fibrin 'miniclots'. To assess the specificity of each antibody, different portions of antibody test solutions were mixed with fibrinogen and also placed on fibrin miniclots. After washing to remove the excess test antibodies, a second indicator antibody was added. This particular antibody bound specifically to the Fab or antigen binding fragment of mouse immunoglobulins and was raidoiodinated to permit quantification of each test antibody.

Cross-Linked Fibrin Assay

To form fully crosslinked human fibrin miniclots, two solutions were needed. The first solution was prepared by mixing 7.50 ml water, 0.100 ml 2M calcium chloride, 0.01 ml of bovine thrombin (Thrombostat, reconstituted with 5 ml of 50% glycerol, Parke-Davis), and 0.100 ml of Factor XIII (1 Unit, reconstituted in 1 ml water as described by Green Cross Corporation, Japan). The second solution was made by dissolving 35 mg of human fibrinogen protein (Kabi, Grade L) in 7 ml of 10% glycerol in water. Miniclots were formed by first pipetting 25 microliters of thrombin-Factor XIIIa solution into each well of a flexible assay plate (Falon Brand, 3911 from Becton-Dickerson). Subsequently, 25 microliters of the fibrinogen solution was added to each, taking special care to underlay this solution by pipetting it at the bottom of each well. Since the fibrinogen solution contained glycerol, it remained largely unmixed with thrombin, but over a 45 minute period a sufficient quantity of the enzyme mix diffused into the fibrinogen layer to catalyze the complete crosslinking of fibrin beneath a layer of fluid. (It was important to avoid direct air exposure of the clot, since this causes increased levels on non-specific binding of test antibodies.) One hour later after the clots had formed, 200 microliters of blocking solution was added to minimize antibody adsorption to walls of each well. This blocking solution was made by mixing 50 ml of gamma-globulin free horse serum (Gibco Laboratories) with 450 ml of a solution with the following composition: 0.05M tris(hydroxymethyl)aminomethane, pH 7.4; 0.14M sodium chloride; 0.003M sodium azide; 0.003M phenylmethylsulfonylflouride; and 20 kallikrein inhibitor units of aprotinin and 20 units of heparin per militer.

After the blocking solution was removed by inverting the flexible assay plates and blotting the excess solution with absorbant paper, 50 microliters of a test solution containing antibody was added to three separate wells to yield data in triplicate. To assess the specificity of each antibody, three test solutions were prepared by mixing equal volumes of a given antibody solution with blocking buffer diluted ten-fold with water, human fibrinogen (Kabi) 2 mg/ml in water, and human fibrinogen at a 8 mg/ml concentration. Fifteen minutes later, solutions containing antibody and negative controls containing buffer only were added to miniclot wells and incubated for 2 hours at room temperature. At the end of this time period, the plate was inverted again to remove the test solutions. Excess antibody was removed by washing miniclots five times with 0.15M sodium chloride. Specifically bound antibody was quantified by adding 50 microliters of radioidoinated goat anti(mouse Fab fragment) containing 75,000 cpm. The specific radioactivity of the probe was approximately 0.6 milliCi per 50 micrograms. After 60 minutes, the excess radioactive antibody was removed by washing five times with 0.15M sodium chloride. Individual wells were separated by cutting with scissors, placed in disposable polycarbonate tubes(Sarsted, 12×75 mm) along with 4 ml of saline. After 18 hrs, the saline was aspirated and the residual radioactivity measured in a gamma counter. The baseline was established by substituting 10% blocking buffer for antibody test solution; this level was usually about 1000 cpm (Micromedics 4/600 AutoGamma Counter). Immunoreactivity was considered significant when the magnitude of binding was greater than twice the magnitude of the baseline standard deviation.

Figure 1:
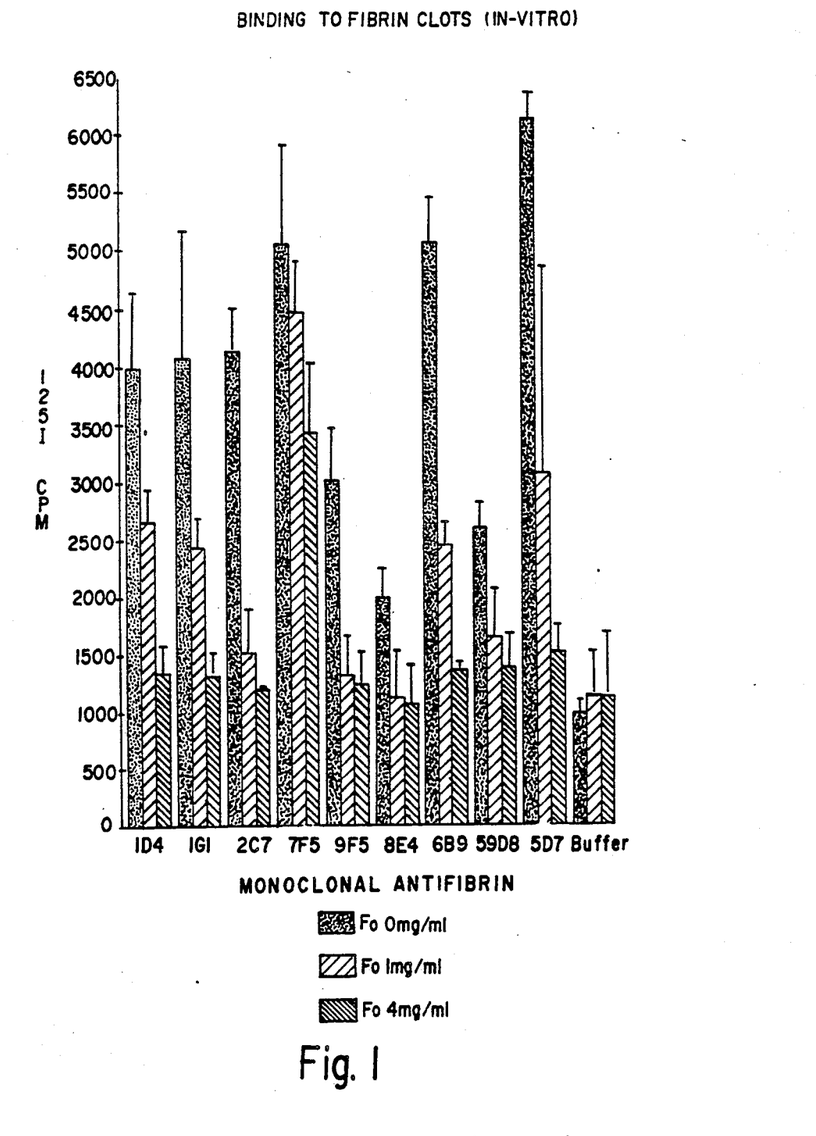
FIG. 1 shows the results from the cross-linked fibrin-clot assay for selection of anti-fibrin antibodies that bind effectively to fully cross-linked fibrin.

An example of a miniclot experiment is shown in FIG. 1. Antibody test solutions were obtained by removing tissue culture media which had been incubated with cloned hybridoma cell lines for at least three days. As described, three separate aliquots of antibody culture supernatant were mixed separately with equal volumes of buffer, 2 mg/ml fibrinogen solution and 8 mg/ml fibrinogen solution. The final concentration of fibrinogen was 0, 1 and 4 mg/ml respectively. After 15 minutes, three 50 microliter aliquots of each mixed solution were pipetted into three wells which contained miniclots. The assay was completed as described and the data used to calculate standard deviations, and plotted as shown in FIG. 1. These particular assay demonstrated, that the antibody named 5D7 bound most avidly to miniclots. The level of binding of 5D7 was nearly twice of 59D8 which is considered the most specific antifibrin antibody derived from a selection process using fibrin monomer instead of miniclots. Data show that in the presence of 1 mg/ml fibrinogen, 59D8 failed to bind significantly to miniclots whereas 5D7 remained bound to miniclots under the same conditions. As compared to 59D8, there were other antibodies which also bound to miniclots such as 1D4, 1G1, 2C7, 6B9, and especially 7F5 which bound to miniclots in the presence of both 1 and 4 mg/ml of fibrinogen.

EXAMPLE II

Figure 2:
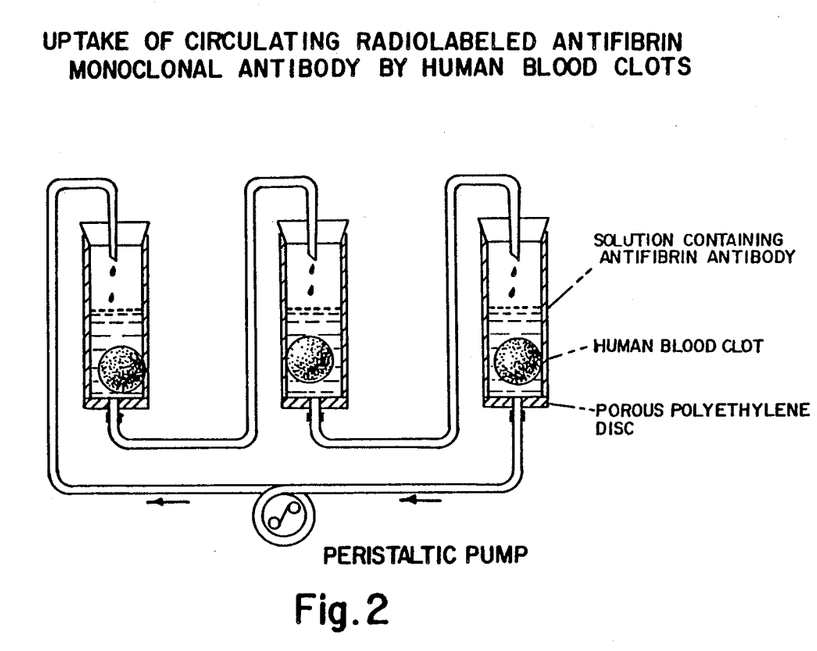
FIG. 2 shows the schematic diagram of the apparatus used for the in vitro screening test.
Figure 3:
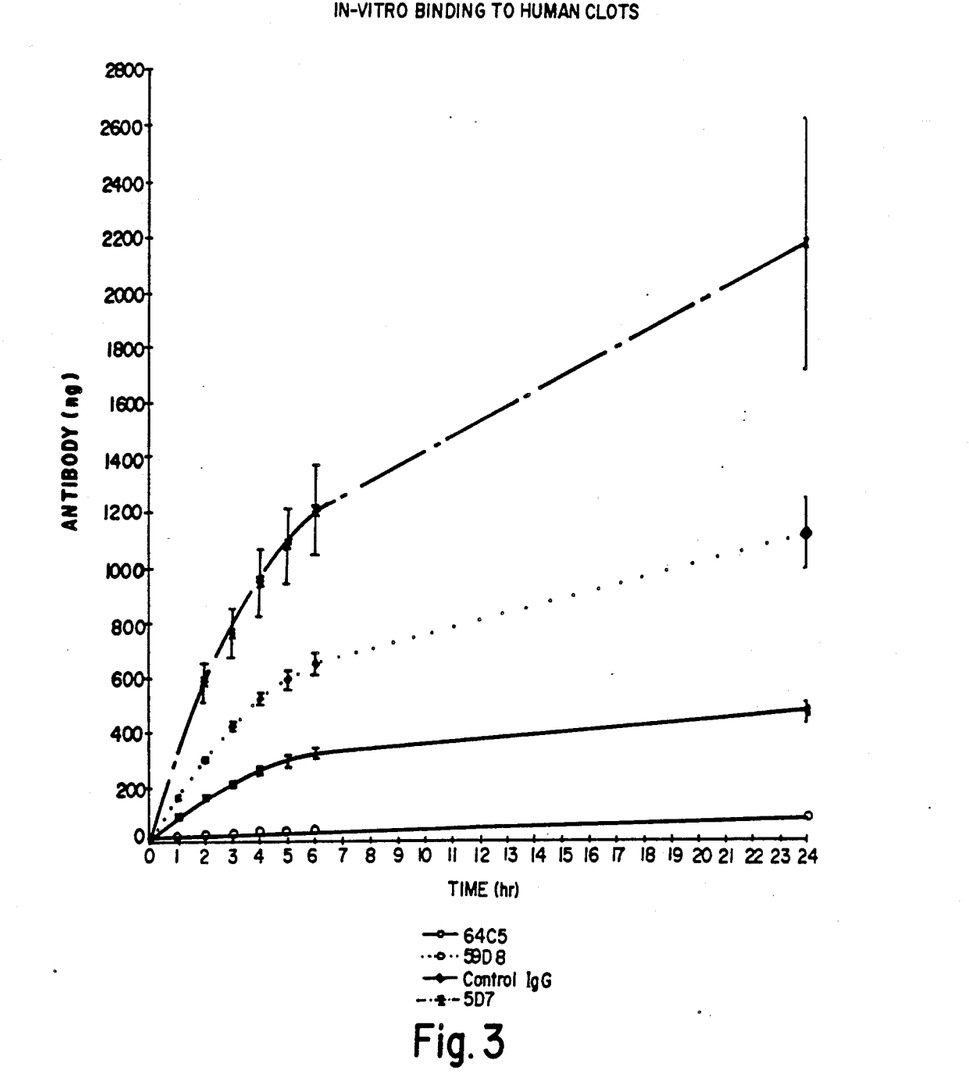
FIG. 3 shows the in vitro binding of anti-fibrin monoclonal antibody to human cross-linked fibrin clot.

Using apparatus shown in FIG. 2, the uptake of radioiodinated antifibrins on human blood clots, was measured as shown in FIG. 3. At the beginning of the experiment, the test antibody solution was added to the system and circulated over three blood clots at 37° C. At different time intervals, clots were removed individually from sample chambers, rinsed with buffer, and counted for 125-iodine. The quantity of antibody bound could be calculated from specific radioactivity of the labeled antibody and the ratio of labeled antibody to the unlabeled antibody which was always 1:19. The formula used for this calculation is provided below. The data in FIG. 3 indicate that antibody bound nearly twice as well as 59D8 and five times better than our reference antibody, 64C5, which has been used by us for localization of blood clots in vivo, Khaw et al., "$^{111}$In Labeled Monoclonal Anti(fibrin specific) Antibody: Detection of Pulmonary Emboli," *J. Nucl. Med.*, 26:P21 (1985). Abstr. These results confirm that an antifibrin selected with a miniclot screening assay binds effectively to an experimental thrombus.

Preparation of Human Blood Clots

Human blood obtained by venipuncture was immediately mixed with aprotinin (Sigma, St. Louis, MO), 100 kallikrein inhibitor units (KIU)/ml of blood. Standard blood clots were formed by dispensing 1.0 ml of blood into 13×100 mm glass test tubes and allowing it to clot. The clots were aged at room temperature for 4 hours, and stored for 18 hr at 4° C. After this aging process, the retracted clot could be transfered by simply inverting the glass test tube.

Radioiodination of Antifibrin Monoclonal Antibodies

Fifty micrograms of antifibrin monoclonal antibody, purified by affinity chromatography against the fibrin-like peptide, beta(1-7) peptide ligand, was radioiodinated with 1 mCi of sodium iodide-125 by the chloramine-T method (Greenwood et al., "The Preparation of $^{131}$I-Labeled Human Growth Hormone of High Specific Radioactivity," *Biochem. J.*, 89:114–23 (1963)). Because protein recovery averaged 75%, the specific radioactivity was calculated after measuring the total radioactivity of the first peak eluted from a bovine albumin-treated G-25 Sephadex column (Pharmacia Inc., Piscataway, NJ).

In Vitro Binding of Antibody to Human Blood Clot

Three plastic chambers (barrels of 12 ml disposable syringes with inner diameter 13 mm, length 66 mm) were fitted with porous polyethylene discs (Cat. No. BB 2062-35A, Bolab, Lake Havasu, Arizona) and connected serially to a peristaltic pump (Isco, Inc., Lincoln, Nebraska). The chambers were rendered airtight by using a rubber stopper. A gauge 19 needle was inserted through each plug and connected via surgical Luer fittings to adjacent chambers with silicon rubber tubing. To minimize binding of radiolabeled antibodies to surfaces, the system was perfused for 18 hrs with horse serum diluted 1:10 with 0.05M tris(hydroxymethyl)aminomethane, 0.15M NaCl, 0.02% NaN$_3$.

At the beginning of the experiment, 7 ml of phosphate buffered saline (PBS: sodium chloride 0.15M, phosphate 0.01M, pH 7.40) containing 700 KIU of aprotinin was added to each chamber. The concentration of the iodinated antifibrin was 60 ng/ml. This was augmented by adding unlabeled antibody so that the final concentration was 1.2 ug/ml. The test antibody solution was then pumped through the chambers at a constant rate, 2 ml/min at 37° C. After the solution had been circulating for 30 minutes, one human blood clot was placed in each chamber.

The radioactivity of the blood clots and the solution was measured with a gamma counter (Micromedic Systems Automatic Gamma Counter Model 4/600, Horsham, Pennsylvania) at the beginning of each experiment, at hourly intervals for the first 6 hours, and finally after 24 hours. At each time interval, the clots were carefully removed from the chambers and washed three times with PBS before counting. To avoid loss of circulating test solution, additional 12 ml syringes were attached to each chamber with two threeway stopcocks. For simplicity these temporary reservoirs are not shown in FIG. 2. After counting, the clots were returned to the chambers for additional incubation. The amount of antibody bound to each clot was calculated using the following formula:

$$\text{Amount of antibody bound to clot} = \text{Counts of the clot} \times \frac{\text{Total amount of antibody added}}{\text{Total initial counts in solution}}$$

EXAMPLE III

Figure 4:
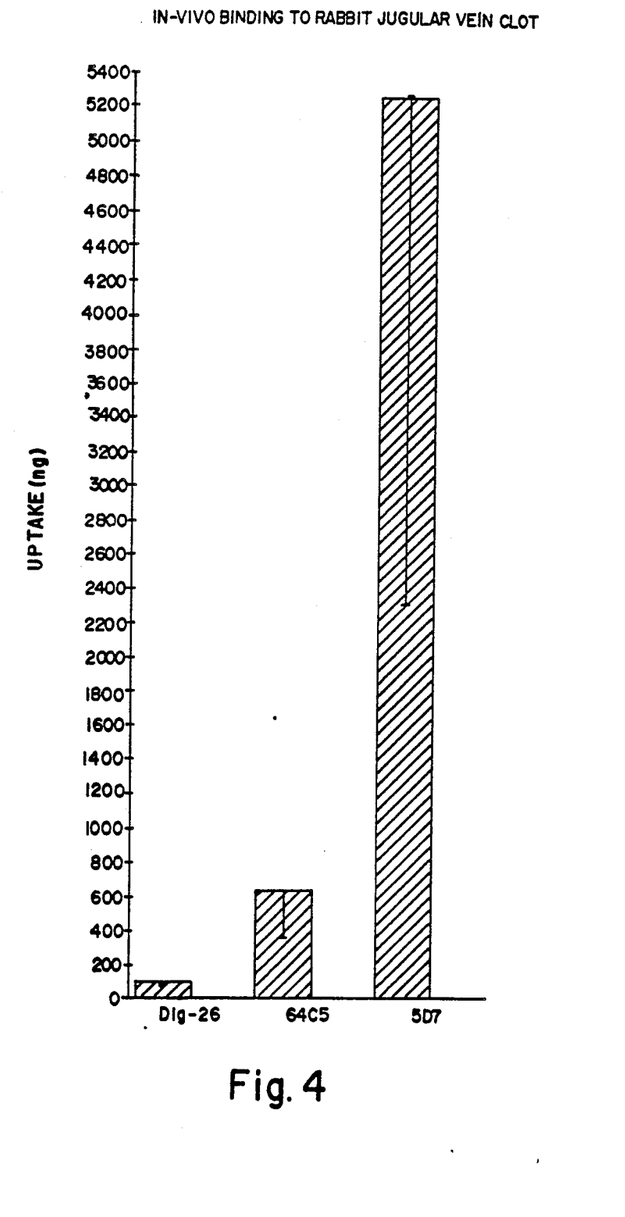
FIG. 4 shows the in vivo localization of a cross-linked fibrin-clot screened monoclonal antibody 5D7 to experimental rabbit thrombi.

In FIG. 4, the uptake of radioactive antifibrin 5D7 was compared to the uptake of antibody 64C5 using an in vivo rabbit model for experimental venous thrombi. The non-specific control antibody was 'Dig-26' a murine monoclonal antibody of irrelevant specificity. This model was adapted from the rabbit thrombosis model described by Collen et al. "Thrombolysis with Human Extrinsic (Tissue-Type) Plasminogen Activator in Rabbits with Experimental Jugular Vein Thrombosis," *J. Clin. Invest.*, 71:368–76 (1983) and is detailed below. Four rabbits were used in each group; error bars relect standard deviation for each group.

In Vivo Antibody Binding

Experiments on rabbits were performed as described by Collen et al. supra, with some modifications. New Zealand White rabbits weighing from 3 to 5 kilograms were anesthetized with intramuscular injections of a 5:1 mixture of ketamine hydroxide (100 mg/ml, Ketalar, Parke-Davis, Morris Plains, NJ) and acepromazine maleate (10 mg/ml), Fort Dodge Laboratories, Inc., Fort Dodge, Iowa). This initial dose of 0.5 ml/kg body weight was followed by hourly supplements at 0.12 ml/kg body weight.

A 5 cm incision was made on one side of neck to expose jugular vein. All branches, except the facial vein, were permanently ligated. The jugular vein was temporarily ligated 3 cm proximal to the facial vein side branch and 2 cm distal. The facial vein was catheterized with a gauge 22 chatheter (Intracath, Deseret Medical Inc., Sandy, Utah). This permitted removal of blood and washing of the isolated jugular vein segment.

Rabbit blood was drawn from marginal ear vein and mixed with human fibrinogen at a ratio of 1 ml of rabbit blood to 1.8 mg of fibrinogen (Grade L, Kabi Diagnostica, Stockholm, Sweden). Ten NIH units of bovine thrombin (1000 units/ml, Thrombostat, Parke-Davis) was injected through the catheter, followed by the rabbit blood - human fibrinogen mixture until the isolated segment was slightly distended. After one hour of incubation to allow for clot maturation, the temporary ligatures on the jugular vein were released.

Antifibrin antibody 64C5 (continuing 2-4% $^{125}$I-64C5) was then injected intravenously via a marginal ear at a dose of 48 ug/kg body weight such that the plasma concentration would be 1.2 ug/ml. Immediately after antibody injection, blood was taken from the contralateral ear vein for counting. After 6 hours, the rabbit was sacrificed and then experimental thrombus rapidly excised from the jugular vein. The clot was freed from the vessel wall, washed in isotonic saline, and counted. Antibody bound to the clot was calculated after taking into account the dilution of labeled antibody with unlabeled antibody. FIG. 4 shows the results of the in vivo antibody binding.

Although the foregoing invention has been described in some detail by way of illustration and example for purposes of clarity of understanding, it will be obvious that certain changes and modifications may be practiced within the scope of the invention, as limited only by the scope of the appended claims.

What is claimed is:

1. A method of screening for hybridomas that secrete human cross-linked fibrin clot-specific monoclonal antibodies consisting essentially of:
   (a) immobilizing a cross-linked human fibrin clot on a solid support or surface;
   (b) contacting said immobilized clot of step (a) with supernatant from a hybridoma cell line capable of secreting monoclonal antibodies against cross-linked fibrin, without fibrinogen cross-reactivity, to form a clot/cross-linked fibrin-specific monoclonal antibody complex; and
   (c) screening for the clot/cross-linked fibrin-specific monoclonal antibody complex by a detectable labeling step to select hybridomas that secrete human cross-linked fibrin clot-specific monoclonal antibodies.

2. The method of claim 1 wherein said detectable labeling step is selected from the group consisting of radioimmunoassays, enzyme immunoassays, fluorescent immunoassays, and chemiluminescent immunoassays.

3. The method of claim 1 wherein said fibrin clot is derived from purified human fibrinogen.

4. The method of claim 3 wherein said clot is derived from freshly drawn human blood or re-calcified citrated blood.

5. A hybridoma cell line that secretes human fibrin clot-specific monoclonal antibodies screened by the method of claim 1.

6. A hybridoma cell line of claim 5 having the identifying characteristics of ATCC No. HB 9087.

7. A cross-linked fibrin clot-specific monoclonal antibody screened by the method of claim 1.

* * * * *